US010023550B2

(12) United States Patent
Stork et al.

(10) Patent No.: US 10,023,550 B2
(45) Date of Patent: Jul. 17, 2018

(54) PRODUCTION OF 2-SUBSTITUTED 4-HYDROXY-4-METHYLTETRAHYDROPYRANS HAVING STABLE ODORIFEROUS QUALITY

(71) Applicant: BASF SE, Ludwigshafen (DE)

(72) Inventors: Timon Stork, Bürstadt Bobstadt (DE); Martine Dehn, Ludwigshafen (DE); Klaus Ebel, Heddesheim (DE); Karl Beck, Östringen (DE); Axel Salden, Stuttgart (DE); Ralf Pelzer, Fürstenberg (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/303,976

(22) PCT Filed: Apr. 8, 2015

(86) PCT No.: PCT/EP2015/057584
§ 371 (c)(1),
(2) Date: Oct. 13, 2016

(87) PCT Pub. No.: WO2015/158586
PCT Pub. Date: Oct. 22, 2015

(65) Prior Publication Data
US 2017/0037021 A1 Feb. 9, 2017

(30) Foreign Application Priority Data
Apr. 14, 2014 (EP) ..................................... 14164594

(51) Int. Cl.
*C07D 319/06* (2006.01)
*C07D 309/10* (2006.01)
*C07C 43/303* (2006.01)
*C07D 309/18* (2006.01)
*C11B 9/00* (2006.01)

(52) U.S. Cl.
CPC .......... *C07D 309/10* (2013.01); *C07C 43/303* (2013.01); *C07D 309/18* (2013.01); *C07D 319/06* (2013.01); *C11B 9/008* (2013.01)

(58) Field of Classification Search
CPC .. C07D 309/10; C07D 309/18; C07D 319/06; C07C 43/303; C11B 9/008
USPC ................... 549/356, 376, 416, 417
See application file for complete search history.

(56) References Cited

U.S. PATENT DOCUMENTS

| 2,471,134 A | 5/1949 | Wright | |
| 4,963,285 A * | 10/1990 | Sprecker | C07D 309/10 252/187.25 |
| 8,546,591 B2 | 10/2013 | Koenigsmann et al. | |
| 8,618,315 B2 * | 12/2013 | Gralla | C07D 309/12 549/423 |
| 2011/0306779 A1 | 12/2011 | Gralla et al. | |
| 2014/0107352 A1 | 4/2014 | Stork et al. | |
| 2014/0163117 A1 | 6/2014 | Rudenauer et al. | |
| 2014/0213494 A1 | 7/2014 | Rudenauer et al. | |
| 2016/0060238 A1 | 3/2016 | Stork et al. | |
| 2016/0068500 A1 | 3/2016 | Stork et al. | |

FOREIGN PATENT DOCUMENTS

| EP | 0122367 A2 | 10/1984 |
| EP | 0770670 A2 | 5/1997 |
| EP | 1493737 A1 | 1/2005 |
| EP | 2991973 A1 | 3/2016 |
| SU | 19752312401 | 12/1975 |
| SU | 573483 A1 | 9/1977 |
| WO | WO-2009077550 A1 | 6/2009 |
| WO | WO 2010/133473 A1 * | 11/2010 |
| WO | WO-2010133473 A1 | 11/2010 |
| WO | WO-2011147919 A1 | 12/2011 |
| WO | WO-2011154330 A1 | 12/2011 |
| WO | WO-2014060345 A1 | 4/2014 |
| WO | WO-2014177484 A1 | 11/2014 |

OTHER PUBLICATIONS

UMASS. Distillation. Accessed May 7, 2017, p. 4424.*
International Search Report for PCT/EP2015/057580 dated Jun. 3, 2015.
International Search Report for PCT/EP2015/057582 dated May 27, 2015.
International Search Report for PCT/EP2015/057584 dated Jun. 15, 2015.
Julia, M., et al., "Synthèse de l'oxyde rose et de composès voisins", Bulletin de la SocietéChimique de France 1963, p. 1983.
Lui, C., et al., "A Novel Synthesis of *cis*-Dihydro-rose Oxide and Related Stereochemistry", Journal of Heterocyclic Chemistry, vol. 21, No. 1, (1984), pp. 129-132.
Romanov, N., et al., "Dehydration of 2- and 2,2-subsituted 4,4-dimethyl- and 4-methyl-4-phenyl-1,3-dioxanes", Journal of Applied Chemistry of the USSR, vol. 55, No. 1, (1982), pp. 140-143. (English translation from Zhurnal Prikladnoi Khimii, Ed. 55, No. 1, (1981), pp. 157-161).
Romanov, N., et al., "Isomerization of 2-R-4,4-dimethyl- and 2-R-4-methyl-4-phenyl-1,3-dioxanes to 2-R-4-methyl- and 2-R-4-phentltetrahydropyran-4-ols", Journal of Applied Chemistry of the USSR, vol. 56, No. 1, (1983), pp. 2526-2528. (English translation from Zhurnal Prikladnoi Khimii, Ed. 55, No. 12, (1982), pp. 2778-2780).
Schindler, G., et al., "Dihydroroseoxide—A Unique New Aroma Chemical", Perfumer & Flavorist, vol. 11, (1986), pp. 29-30.
U.S. Appl. No. 15/304,299, filed Oct. 14, 2016, Stork et al.
U.S. Appl. No. 15/304,283, filed Oct. 14, 2016, Rüdenauer et al.

(Continued)

*Primary Examiner* — Taylor V Oh
(74) *Attorney, Agent, or Firm* — Drinker Biddle & Reath LLP

(57) ABSTRACT

The present invention relates to a method for the production of 2-substituted 4-hydroxy-4-methyltetrahydropyrans from the acid-catalyzed reaction of 3-methylbut-3-ene-1-ol with an aldehyde, a stable odoriferous quality being achieved and avoiding off-odors that interfere with the odor sensation.

22 Claims, No Drawings

(56) References Cited

OTHER PUBLICATIONS

International Preliminary Report on Patentability for Application No. PCT/EP2015/057580, English Translation, dated Sep. 5, 2016.
International Preliminary Report on Patentability for Application No. PCT/EP2015/057582, English Translation, dated Oct. 18, 2016.
International Preliminary Report on Patentability for Application No. PCT/EP2015/057584, English Translation, dated Aug. 2, 2016.
Wüst, et al., "Structure Elucidation, Enantioselective Analysis, and Biogenesis of Nerol Oxide in Pelargonium Species", J. Agric. Food Chem., vol. 47, pp. 3145-3150 (1999).

* cited by examiner

PRODUCTION OF 2-SUBSTITUTED 4-HYDROXY-4-METHYLTETRAHYDROPYRANS HAVING STABLE ODORIFEROUS QUALITY

CROSS-REFERENCE TO RELATED APPLICATIONS

This application is a national stage application (under 35 U.S.C. § 371) of PCT/EP2015/057584, filed Apr. 8, 2015, which claims benefit of European Application No. 14164594.5, filed Apr. 14, 2014, both of which are incorporated herein by reference in their entirety.

BACKGROUND OF THE INVENTION

The present invention relates to a process for the preparation of 2-substituted 4-hydroxy-4-methyltetrahydropyrans from the acid-catalyzed reaction of 3-methylbut-3-en-1-ol with an aldehyde, where a stable fragrance quality is attained without the odor impression of troublesome off-notes.

PRIOR ART

2-Substituted 4-hydroxy-4-methyltetrahydropyrans are valuable compounds for use as aroma chemicals. Thus, for example, the cis/trans-diastereomer mixture of 2-(2-methylpropyl)-4-hydroxy-4-methyltetrahydropyran

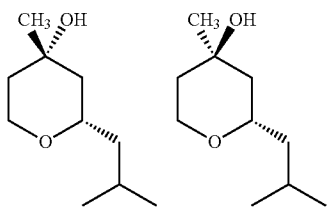

is characterized by a pleasant lily of the valley scent and is suitable to a particular degree for use as aroma chemical, e.g. for producing fragrance compositions.

EP 1 493 737 A1 discloses a process for the preparation of mixtures of ethylenically unsaturated 4-methyl- or 4-methylenepyrans and the corresponding 4-hydroxypyrans by reacting the corresponding aldehydes with isoprenol, where the reaction is initiated in a reaction system in which the molar ratio of aldehyde to isoprenol is greater than 1, i.e. the aldehyde is used in excess. Moreover, the document discloses the subsequent dehydration of said mixtures to the desired ethylenically unsaturated pyrans.

WO 2011/147919 describes a process for the preparation of 2-substituted 4-hydroxy-4-methyltetrahydropyranols and specifically of 2-isobutyl-4-hydroxy-4-methyltetrahydropyran by reacting isoprenol with prenal and subsequent hydrogenation.

WO 2010/133473 describes a process for the preparation of 2-substituted 4-hydroxy-4-methyltetrahydropyrans of the formula (A)

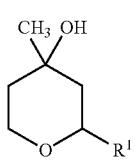

(A)

where the radical $R^1$ is a straight-chain or branched alkyl or alkenyl radical having 1 to 12 carbon atoms, an optionally alkyl-substituted cycloalkyl radical having in total 3 to 12 carbon atoms or an optionally alkyl- and/or alkoxy-substituted aryl radical having in total 6 to 12 carbon atoms, in which isoprenol (3-methylbut-3-en-1-ol) is reacted with an aldehyde of the formula $R^1$—CHO, where the reaction is carried out in the presence of water and in the presence of a strongly acidic cation exchanger.

WO 2011/154330 describes a process comparable to WO 2010/133473, where the resulting reaction mixture is subjected to a distillative processing in a dividing-wall column or in two thermally coupled distillation columns.

As is described in WO 2010/133473 and WO 2011/154330, during the acid-catalyzed reaction of isoprenol (3-methylbut-3-en-1-ol) with an aldehyde of the formula $R^1$—CHO, a complex reaction mixture is formed which, besides 2-substituted 4-hydroxy-4-methyltetrahydropyrans, also comprises dehydrated by-products of the formulae (D), (E) and/or (F)

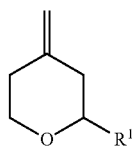

(D)

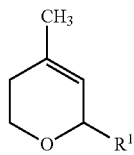

(E)

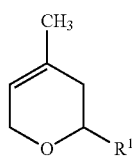

(F)

and also, as further by-products, inter alia the 1,3-dioxanes (G)

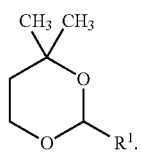

(G)

The unpublished international patent application PCT/EP2013/071409 describes a process for the preparation of 2-substituted 4-hydroxy-4-methyltetrahydropyrans of the general formula (A) and of 2-substituted 4-methyltetrahydropyrans of the general formula (B)

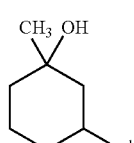

(A)

(B)

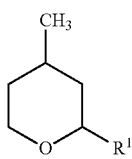

in which
R[1] is straight-chain or branched $C_1$-$C_{12}$-alkyl, straight-chain or branched $C_2$-$C_{12}$-alkenyl, unsubstituted or $C_1$-$C_{12}$-alkyl- and/or $C_1$-$C_{12}$-alkoxy-substituted cycloalkyl having in total 3 to 20 carbon atoms or unsubstituted or $C_1$-$C_{12}$-alkyl- and/or $C_1$-$C_{12}$-alkoxy-substituted aryl having in total 6 to 20 carbon atoms,
in which
a) 3-methylbut-3-en-1-ol is reacted with an aldehyde of the formula R[1]—CHO, where R[1] in the formula has the meaning given above, in the presence of an acidic catalyst, where a reaction mixture is obtained which comprises at least one 2-substituted 4-hydroxy-4-methyltetrahydropyran of the general formula (A), at least one of the compounds (D), (E) or (F) and at least one dioxane compound (G)

(D)

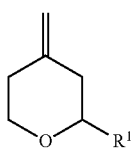

(E)

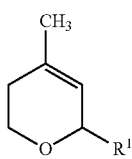

(F)

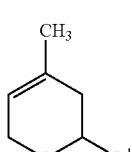

(G)

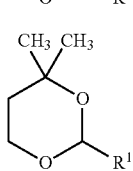

where R[1] has the meaning given above,
b) the reaction product from step a) is subjected to a separation to give a fraction enriched in 2-substituted 4-hydroxy-4-methyltetrahydropyrans of the general formula (A) and a fraction which comprises at least one of the compounds (D), (E) or (F) and at least one dioxane compound (G),
c) the fraction which comprises at least one of the compounds (D), (E) or (F) and at least one dioxane compound (G) is subjected to a hydrogenation,
d) from the hydrogenation product obtained in step c) a fraction enriched in 2-substituted 4-methyltetrahydropyrans (B) and a fraction enriched in at least one dioxane compound (G) are isolated.

Romanov et al. describe in the Journal of Applied Chem. of the USSR, 55(1), p. 140-143 (1982) (English translation from Zhurnal Prikladnoi Khimii, Vol. 55, No. 1, 157-161 (1981)) the acid-catalyzed reaction of the dioxane compound G') to the dihydropyrans E') and F').

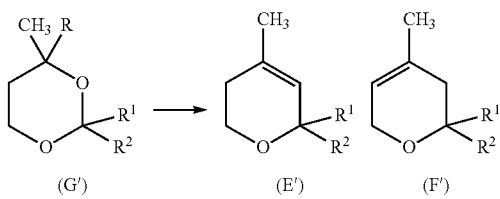

The table mentions 4-methyl-2-isobutyl-5,6-dihydropyran and 4-methyl-2-isobutyl-3,6-dihydropyran. The acidic catalysts used are $H_2SO_4$ or sulfonic acid group-containing styrene-divinylbenzene ion exchangers. The reaction takes place with dioxane compounds G') in pure form and in the presence of cyclohexane or toluene as solvent. Romanov et al. describe in the Journal of Applied Chem. of the USSR, 56 (1), p. 2526-2528 (1983) (English translation from Zhurnal Prikladnoi Khimii, Vol. 55, No. 12, 2778-2780 (1982)) the acid-catalyzed isomerization of 2-R-4,4-dimethyl- and 2-R-4-methyl-4-phenyl-1,3-dioxanes to 2-R-4,4-methyl- and 2-R-4-phenyl-1,3-tetrahydropyran-4-ols.

An essential requirement placed on the synthesis of aroma chemicals and specifically on odor substances is the consistently high quality of the product. An essential quality criterion is that a stable fragrance quality is attained without the odor impression of troublesome off-notes. In this connection, neither in the case of production in a batch process must individual batches have undesired odor notes, nor, in the case of continuous production must the fragrance quality deteriorate in the course of production. The latter can be attributed for example to aging processes of the catalyst used and changes in the product spectrum associated therewith. Specifically in the case of the preparation of 2-substituted 4-hydroxy-4-methyltetrahydropyrans from the acid-catalyzed reaction of 3-methylbut-3-en-1-ol with an aldehyde, it is sometimes observed that the fragrance quality, specifically of the formulated end product following prolonged storage no longer corresponds to the expectation. In these cases, the product often has an undesired cheesy odor note. The object of the present invention is to provide an improved process for the preparation of 2-substituted 4-hydroxy-4-methyltetrahydropyrans which reduces or avoids this problem.

Surprisingly, it has now been found that this object is achieved if the reaction product obtained during the acid-catalyzed reaction of 3-methylbut-3-en-1-ol with an aldehyde for the preparation of 2-substituted 4-hydroxy-4-methyltetrahydropyrans, prior to its distillative separation, is brought into contact with an acidic ion exchanger and/or admixed with a strong acid. This acid treatment can reliably avoid the formation of troublesome odor notes. This is particularly surprising since the preparation according to the invention of the 2-substituted 4-hydroxy-4-methyltetrahydropyrans already takes place in the presence of an acidic catalyst.

SUMMARY OF THE INVENTION

The invention provides a process for the preparation of 2-substituted 4-hydroxy-4-methyltetrahydropyrans of the general formula (I)

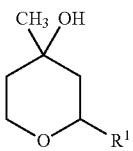

(I)

in which
R$^1$ is straight-chain or branched C$_1$-C$_{12}$-alkyl, straight-chain or branched C$_2$-C$_{12}$-alkenyl, unsubstituted or C$_1$-C$_{12}$-alkyl- and/or C$_1$-C$_{12}$-alkoxy-substituted cycloalkyl having in total 3 to 20 carbon atoms or unsubstituted or C$_1$-C$_{12}$-alkyl- and/or C$_1$-C$_{12}$-alkoxy-substituted aryl having in total 6 to 20 carbon atoms,
in which
a) 3-methylbut-3-en-1-ol of the formula (IV)

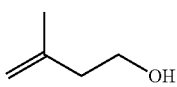

(IV)

is reacted with an aldehyde of the formula (V)

R$^1$—CHO (V)

in which
R$^1$ is straight-chain or branched C$_1$-C$_{12}$-alkyl, straight-chain or branched C$_2$-C$_{12}$-alkenyl, unsubstituted or C$_1$-C$_{12}$-alkyl- and/or C$_1$-C$_{12}$-alkoxy-substituted cycloalkyl having in total 3 to 20 carbon atoms or unsubstituted or C$_1$-C$_{12}$-alkyl- and/or C$_1$-C$_{12}$-alkoxy-substituted aryl having in total 6 to 20 carbon atoms,
in the presence of an acidic catalyst, where a reaction mixture is obtained which comprises at least one 2-substituted 4-hydroxy-4-methyltetrahydropyran of the general formula (I),
b) the reaction mixture from step a) is subjected to a distillative separation to give at least one fraction enriched in the 2-substituted 4-hydroxy-4-methyltetrahydropyrans of the general formula (I),
where the reaction mixture from step a), prior to use in step b) and/or during use in step b), is brought into contact with an acidic ion exchanger and/or admixed with a strong acid.

The invention further provides 2-substituted 4-hydroxy-4-methyltetrahydropyrans of the general formula (I) which are obtainable by the process defined above and below. This is in particular 2-isobutyl-4-hydroxy-4-methyltetrahydropyran.

The 2-substituted 4-hydroxy-4-methyltetrahydropyrans of the general formula (I) obtained by the process according to the invention, in particular 2-isobutyl-4-hydroxy-4-methyltetrahydropyran, are advantageously suitable for use as aroma chemical, specifically as fragrance.

DESCRIPTION OF THE INVENTION

Unless stated more precisely hereinbelow, the terms "2-substituted 4-hydroxy-4-methyltetrahydropyran" and "2-(2-methylpropyl)-4-hydroxy-4-methyltetrahydropyran" in the context of the invention refer to cis/trans mixtures of any composition, and also to the pure conformational isomers. The aforementioned terms further refer to all enantiomers in pure form, as well as racemic and optionally active mixtures of the enantiomers of these compounds.

Wherever the discussion hereinbelow is of cis and trans diastereomers of the compounds (I), in each case only one of the enantiomeric forms is depicted. Merely for the purposes of illustration, the isomers of 2-(2-methylpropyl)-4-hydroxy-4-methyltetrahydropyran (I) are given below:

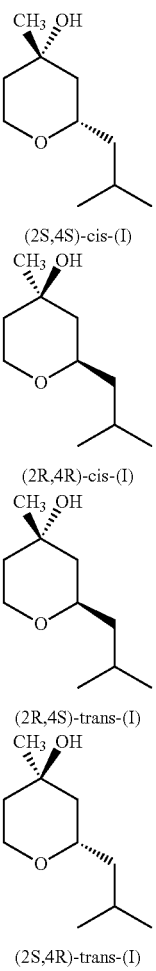

In the context of the present invention, the expression straight-chain or branched alkyl preferably stands for C$_1$-C$_6$-alkyl and particularly preferably for C$_1$-C$_4$-alkyl. Alkyl is in particular methyl, ethyl, n-propyl, isopropyl, n-butyl, isobutyl (2-methylpropyl), sec-butyl (1-methylpropyl), tert-butyl (1,1-dimethylethyl), n-pentyl or n-hexyl. Specifically, alkyl is methyl, ethyl, n-propyl, isopropyl, or isobutyl.

In the context of the present invention, the expression straight-chain or branched alkoxy preferably stands for C$_1$-C$_6$-alkoxy and particularly preferably for C$_1$-C$_4$-alkoxy. Alkoxy is in particular methoxy, ethoxy, n-propyloxy, isopropyloxy, n-butyloxy, isobutyloxy, sec-butyloxy, tert-butyloxy, n-pentyloxy or n-hexyloxy. Specifically, alkoxy is methoxy, ethoxy, n-propyloxy, isopropyloxy, or isobutyloxy.

In the context of the present invention, the expression straight-chain or branched alkenyl preferably stands for C$_2$-C$_6$-alkenyl and particularly preferably for C$_2$-C$_4$-alkenyl Besides single bonds, the alkenyl radical also has one or more, preferably 1 to 3, particularly 1 or 2 and very particularly preferably one, ethylenic double bond. Alkenyl is in particular ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl.

In the context of the invention, cycloalkyl refers to a cycloaliphatic radical having preferably 3 to 10, particularly preferably 5 to 8, carbon atoms. Examples of cycloalkyl groups are in particular cyclopropyl, cyclobutyl, cyclopentyl, cyclohexyl, cycloheptyl or cyclooctyl. Specifically, cycloalkyl is cyclohexyl.

Substituted cycloalkyl groups can have one or more (e.g. 1, 2, 3, 4 or 5) substituents depending on the ring size. These are preferably selected independently of one another from $C_1$-$C_6$-alkyl and $C_1$-$C_6$-alkoxy. In the case of a substitution, the cycloalkyl groups carry preferably one or more, for example one, two, three, four or five $C_1$-$C_6$-alkyl groups. Examples of substituted cycloalkyl groups are in particular 2- and 3-methylcyclopentyl, 2- and 3-ethylcyclopentyl, 2-, 3- and 4-methylcyclohexyl, 2-, 3- and 4-ethylcyclohexyl, 2-, 3- and 4-propylcyclohexyl, 2-, 3- and 4-isopropylcyclohexyl, 2-, 3- and 4-butylcyclohexyl and 2-, 3- and 4-isobutylcyclohexyl.

In the context of the present invention, the expression "aryl" comprises mono- or polynuclear aromatic hydrocarbon radicals having usually 6 to 18, preferably 6 to 14, or particularly preferably 6 to 10, carbon atoms. Examples of aryls are in particular phenyl, naphthyl, indenyl, fluorenyl, anthracenyl, phenanthrenyl, naphthacenyl, chrysenyl, pyrenyl, etc., and specifically phenyl or naphthyl.

Substituted aryls can have one or more (e.g. 1, 2, 3, 4 or 5) substituents depending on the number and size of their ring systems. These are preferably selected independently of one another from $C_1$-$C_6$-alkyl and $C_1$-$C_6$-alkoxy. Examples of substituted aryl radicals are 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethyl-phenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutyl-phenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl and 2,4,6-tri-tert-butylphenyl.

Preferably, $R^1$ in the compounds of the formulae (I), (II), (III.1), (III.2), (III.3), (V), and (VI) is straight-chain or branched $C_1$-$C_{12}$-alkyl or straight-chain or branched $C_2$-$C_{12}$-alkenyl. Particularly preferably, $R^1$ is straight-chain or branched $C_1$-$C_6$-alkyl or straight-chain or branched $C_2$-$C_6$-alkenyl. In a further preferred embodiment, $R^1$ is phenyl.

Meanings for the radical $R^1$ that are preferred according to the invention are therefore, for example, methyl, ethyl, n-propyl, isopropyl, n-butyl, isobutyl, n-pentyl, n-hexyl or n-heptyl, preferably methyl, ethyl, n-propyl, isopropyl, n-butyl, isobutyl, very particularly preferably isobutyl (2-methylpropyl).

Consequently, in the context of one preferred embodiment, the present invention relates to a process for the preparation and isolation of 2-(2-methylpropyl)-4-hydroxy-4-methyltetrahydropyran of the formula (Ia).

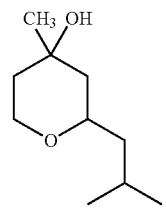

(I.a)

Step a)

One of the starting materials for step a) of the process according to the invention is 3-methylbut-3-en-1-ol (isoprenol) of the formula (IV),

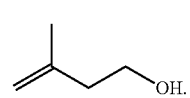

(IV)

Isoprenol is readily accessible by known processes from isobutene and formaldehyde on every scale and is commercially available. No particular requirements are placed on the purity, quality or preparation process of the isoprenol to be used according to the invention. It can be used in standard commercial quality and purity in step a) of the process according to the invention. Preference is given to using isoprenol which has a purity of 90% by weight or above, particularly preferably one with a purity of 95 to 100% by weight and very particularly preferably of from 97 to 99.9% by weight, or even more preferably 98 to 99.8% by weight.

A further starting material for step a) of the process according to the invention is an aldehyde of the formula (V) $R^1$—CHO, where $R^1$ has the meaning given above in formula (V).

Preferably, $R^1$ in the compounds of the formula (V) is straight-chain or branched $C_1$-$C_{12}$-alkyl or straight-chain or branched $C_2$-$C_{12}$-alkenyl. Particularly preferably, $R^1$ is straight-chain or branched $C_1$-$C_6$-alkyl or straight-chain or branched $C_2$-$C_6$-alkenyl. In a further preferred embodiment, $R^1$ is phenyl.

Meanings for the radical $R^1$ that are preferred according to the invention are thus, for example, methyl, ethyl, n-propyl, isopropyl, n-butyl, isobutyl, n-pentyl, n-hexyl or n-heptyl, preferably methyl, ethyl, n-propyl, isopropyl, n-butyl, isobutyl, very particularly preferably isobutyl (2-methylpropyl).

Aldehydes of the formula (V) to be used with preference are: acetaldehyde, valeraldehyde, isovaleraldehyde, pentanal, hexanal, heptanal, benzaldehyde, citral, citronellal. Aldehydes of the formula (V) that are to be used with very particular preference according to the invention are isovaleraldehyde and benzaldehyde, in particular isovaleraldehyde.

Preferably, in step a), the 3-methylbut-3-en-ol (IV) and the aldehyde (V) are used in a molar ratio of about 1:2 to 2:1, particularly preferably from 0.7:1 to 2:1, in particular from 1:1 to 2:1. In a specific embodiment, in step a), the 3-methylbut-3-en-ol (III) and the aldehyde (V) are used in a molar ratio of from 1:1 to 1.5:1.

According to the invention, the reaction in step a) takes place in the presence of an acidic catalyst. In principle, for the reaction in step a) any acidic catalyst can be used, i.e. any substance which has Brönstedt or Lewis acidity. Examples of suitable catalysts are protic acids, such as hydrochloric acid, sulfuric acid, phosphoric acid, methanesulfonic acid and p-toluenesulfonic acid, acidic molecular element compounds, such as aluminum chloride, boron trifluoride, zinc chloride, phosphorus pentafluoride, arsenic trifluoride, tin tetrachloride, titanium tetrachloride and antimony pentafluoride; oxidic acidic solid bodies such as zeolites, silicates, aluminates, alumosilicates, clays and acidic ion exchangers.

Preferably, the acidic catalyst used in step a) is selected from hydrochloric acid, sulfuric acid, methanesulfonic acid, p-toluenesulfonic acid and strongly acidic cation exchangers.

In a first variant, the reaction in step a) takes place in the presence of a Brönstedt acid, which is preferably selected from hydrochloric acid, sulfuric acid, methanesulfonic acid, p-toluenesulfonic acid. In this first variant, in step a) a solvent can be used which is preferably selected from hydrocarbons and hydrocarbon mixtures. Suitable solvents are, for example, hexane, heptane, ligroin, petroleum ether, cyclohexane, decalin, toluene, xylene and mixtures thereof. Preference is given to using no solvent. Preferably, the catalyst in this first variant is used in an amount of from 0.05 to 5 mol %, particularly preferably from 0.1 to 4 mol %, based on the aldehyde (V). Preferably, the reaction in step a) according to this first variant takes place at a temperature in the range from 20 to 120° C., particularly preferably 30 to 80° C.

In a second variant, the reaction in step a) takes place in the presence of a strongly acidic cation exchanger. The term strongly acidic cation exchanger here is understood as meaning a cation exchanger in the H$^+$ form which has strongly acidic groups. The strongly acidic groups are generally sulfonic acid groups. The acidic groups are generally bonded to a polymer matrix, which may be e.g. gel-like and/or macroporous. A preferred embodiment of the process according to the invention is accordingly characterized in that a strongly acidic cation exchanger that has sulfonic acid groups is used. Suitable strongly acidic cation exchangers are described in WO 2010/133473 and WO 2011/154330, to which reference is made here in its entirety.

Of suitability for use in step a) are strongly acidic ion exchangers (such as e.g. Amberlyst, Amberlite, Dowex, Lewatit, Purolite, Serdolit), which are based on polystyrene and which comprise copolymers of styrene and divinylbenzene as carrier matrix with sulfonic acid groups in H$^+$ form, as well as ion exchanger groups functionalized with sulfonic acid groups (—SO$_3$H). The ion exchangers differ in the structure of their polymeric backbones, and a distinction is made between gel-like and macroporous resins. In a specific embodiment, in step a) a perfluorinated polymeric ion exchanger resin is used. Resins of this type are sold e.g. under the name Nafion® by DuPont. An example of such a perfluorinated polymeric ion exchanger resin which may be mentioned is Nafion® NR-50.

Commercially available strongly acidic cation exchangers suitable for the reaction in step a) are known for example under the trade names Lewatit® (Lanxess), Purolite® (The Purolite Company), Dowex® (Dow Chemical Company), Amberlite® (Rohm and Haas Company), Amberlyst™ (Rohm and Haas Company). Preferred strongly acidic cation exchangers are: Lewatit® K 1221, Lewatit® K 1461, Lewatit® K 2431, Lewatit® K 2620, Lewatit® K 2621, Lewatit® K 2629, Lewatit® K 2649, Amberlite® FPC 22, Amberlite® FPC 23, Amberlite® IR 120, Amberlyst™ 131, Amberlyst™ 15, Amberlyst™ 31, Amberlyst™ 35, Amberlyst™ 36, Amberlyst™ 39, Amberlyst™ 46, Amberlyst™ 70, Purolite® SGC650, Purolite® C100H, Purolite® C150H, Dowex® 50X8, Serdolit® red and Nation® NR-50.

The strongly acidic ion exchanger resins are usually regenerated with hydrochloric acid and/or sulfuric acid.

In a specific embodiment, in step a) the 3-methylbut-3-en-ol (IV) and the aldehyde (V) are reacted in the presence of a strongly acidic cation exchanger and in the presence of water. According to a specific embodiment, besides isoprenol (IV) and the aldehyde of the formula (V), water is also additionally added to the reaction mixture.

In a suitable embodiment, the starting materials are reacted in the presence of at least mol %, preferably of at least 50 mol %, of water. For example, the starting materials are reacted in the presence of from 25 to 150 mol %, preferably from 40 to 150 mol %, particularly preferably from 50 to 140 mol %, in particular from 50 to 80 mol %, of water. Here, the amount of water used refers to the quantitative amount of the starting material optionally used in deficit or, in the case of an equimolar reaction, to the quantitative amount of one of the two.

Preferably, the reaction is carried out in the presence of about at least 3% by weight, particularly preferably of at least 5% by weight, of added water. The alcohol of the formula (IV) and the aldehyde of the formula (V) are reacted for example in the presence of 3% by weight to 15% by weight of water, preferably from 5% by weight to 12% by weight of water. The percentages by weight given above here are based on the total amount of the reaction mixture, consisting of the components of the formulae (IV) and (V), and also water.

Above the stated value, the amount of water can be freely chosen and is limited only by processing or cost aspects, if at all, and can moreover be used in a large excess, for example in a 5- to 15-fold excess, or even more. Preferably, a mixture of isoprenol (IV) and the aldehyde of the formula (V), preferably isovaleraldehyde, with the amount of water to be added is prepared such that the added water remains dissolved in the mixture of isoprenol and the aldehyde, i.e. a two-phase system is not present.

For the reaction of isoprenol (IV) with the aldehyde (V) in step a), the stated starting materials and optionally the added water can be brought into contact with the acidic cation exchanger. Preferably, isoprenol (IV), aldehyde (V) and optionally the added water are used in the form of a mixture in step a). The stated starting materials, i.e. isoprenol (IV) and the aldehyde (V) and the water to be used in the above amount can be brought into contact with one another and/or mixed in any desired order.

The amount of strongly acidic cation exchanger in step a) is not critical and can be selected freely within wide limits taking into consideration the economic and processing aspect. The reaction can accordingly be carried out either in the presence of catalytic amounts or else in the presence of large excesses of the strongly acidic cation exchanger. Usually, the strongly acidic cation exchanger is used in an amount of from about 5 to about 40% by weight, preferably in an amount of from about 20 to about 40% by weight and particularly preferably in an amount of from about 20 to about 30% by weight, in each case based on the sum of used isoprenol (IV) and aldehyde of the formula (V). Here, the data refer to the ready-to-use cation exchanger, which is generally pretreated with water and accordingly can comprise amounts of up to about 70% by weight, preferably of from about 30 to about 65% by weight and particularly preferably from about 40 to about 65% by weight, of water. Particularly in the case of a discontinuous procedure, an addition of water over and above this can therefore be superfluous when carrying out the process according to the invention. The specified strongly acidic cation exchangers can be used in step a) either individually or else in the form of mixtures.

In the case of a continuous procedure, the catalyst hourly space velocity is for example in the range from 50 to 2500 mol per m³ of catalyst and h, preferably in the range from 100 to 2000 mol per m³ of catalyst and h, in particular in the range from 130 to 1700 mol per m³ of catalyst and h, where the quantitative amount in mol refers to the starting material of the formula (IV).

The reaction in step a) in the presence of a strongly acidic cation exchanger can if desired also be additionally carried out in the presence of a solvent that is inert under the reaction conditions. Suitable solvents are, for example, tert-butyl methyl ether, cyclohexane, decalin, hexane, heptane, ligroin, petroleum ether, toluene and xylene. The stated solvents can be used alone or in the form of mixtures with one another. Preferably, the reaction in step a) is carried out in the presence of a strongly acidic cation exchanger without addition of an organic solvent.

Preferably, the reaction of isoprenol (IV) with the selected aldehyde (V) in step a) is carried out in the presence of water and in the presence of a strongly acidic cation exchanger at a temperature in the range from 0 to 70° C., particularly preferably at a temperature in the range from 20 to 70° C. and in particular at a temperature in the range from 20 to 60° C. This is the temperature of the reaction mixture.

The reaction in step a) can be carried out discontinuously or continuously. Here, for example in the discontinuous case, the reaction can be performed such that a mixture of isoprenol (IV), the aldehyde (V), optionally water and optionally an organic solvent is charged to a suitable reaction vessel, and the acidic catalyst is added. When the reaction is complete, the catalyst can then be separated off from the resulting reaction mixture by suitable separation processes. The order in which the individual reaction components are brought into contact is not critical and can be varied according to the scale of the particular processing configuration. If a Brönstedt acid, which is preferably selected from hydrochloric acid, sulfuric acid, methanesulfonic acid, p-toluenesulfonic acid, is used as catalyst in step a), then the separating off of the catalyst can take place distillatively e.g. following aqueous work-up or take place directly by distillation. If a strongly acidic cation exchange is used as catalyst in step a), then the separating off of the catalyst can take place e.g. by filtration or by centrifugation.

In the context of a preferred embodiment, the reaction of isoprenol (IV) with the aldehyde (V) in step a) is carried out continuously. For this, for example a mixture of the starting materials to be reacted of isoprenol and aldehyde of the formula (V) with water can be prepared and this mixture can then continuously be brought into contact with a strongly acidic cation exchanger. For this, the selected cation exchanger can be introduced for example into a suitable through-flow reactor, for example a stirred reactor with feed and discharge or a tubular reactor, and the starting materials and the water can be introduced into these continuously and the reaction mixture can be discharged continuously. Here, the starting materials and the water can be introduced as desired into the through-flow reactor as individual components or else in the form of a mixture as described above. Corresponding processes are described in the European patent applications 13165767.8 and 13165778.5.

In step a) of the process according to the invention a reaction mixture is obtained which comprises at least one 2-substituted 4-hydroxy-4-methyltetrahydropyran of the general formula (I)
at least one dioxane compound (II)

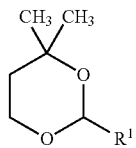

(II)

and at least one of the compounds (III.1), (III.2) or (III.3)

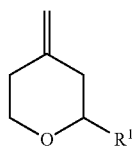

(III.1)

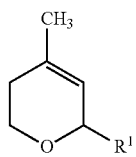

(III.2)

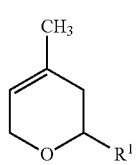

(III.3)

in which
$R^1$ is straight-chain or branched $C_1$-$C_{12}$-alkyl, straight-chain or branched $C_2$-$C_{12}$-alkenyl, unsubstituted or $C_1$-$C_{12}$-alkyl- and/or $C_1$-$C_{12}$-alkoxy-substituted cycloalkyl having in total 3 to 20 carbon atoms or unsubstituted or $C_1$-$C_{12}$-alkyl- and/or $C_1$-$C_{12}$-alkoxy-substituted aryl having in total 6 to 20 carbon atoms.

Preferably, $R^1$ is isobutyl. As a rule, the reaction mixture comprises a mixture of the compounds (III.1), (III.2) and (III.3).

The reaction mixture obtained in step a) of the process according to the invention can comprise at least one compound which is preferably selected from:
3-methylbut-3-en-1-ols of the formula (IV)
aldehydes of the formula (V)
acetals of the general formula (VI)

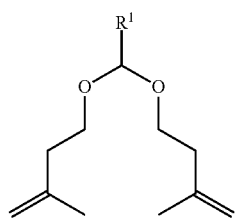

(VI)

in which
$R^1$ is straight-chain or branched $C_1$-$C_{12}$-alkyl, straight-chain or branched $C_2$-$C_{12}$-alkenyl, unsubstituted or $C_1$-$C_{12}$- alkyl- and/or $C_1$-$C_{12}$-alkoxy-substituted cycloalkyl having in total 3 to 20 carbon atoms or unsubstituted or $C_1$-$C_{12}$-alkyl- and/or $C_1$-$C_{12}$-alkoxy-substituted aryl having in total 6 to 20 carbon atoms.

Preferably, $R^1$ is isobutyl.

The reaction mixture obtained in step a) of the process according to the invention can comprise further components, such as water, organic solvent, etc.

Preferably, the reaction mixture obtained in step a) comprises the 2-substituted 4-hydroxy-4-methyltetrahydropyran of the formula (I) in an amount of from 50 to 90% by weight, particularly preferably 60 up to about 80% by weight, based on the total weight of the reaction mixture.

Preferably, the reaction mixture obtained in step a) comprises the dioxane compound of the formula (II) in a total amount of from 5 to 20% by weight, particularly preferably 5 up to about 15% by weight, based on the total weight of the reaction mixture. Preferably, the reaction mixture obtained in step a) comprises the compounds of the formulae (III.1), (III.2) and (III.3) in a total amount of from 5 to 20% by weight, particularly preferably 5 up to about 15% by weight, based on the total weight of the reaction mixture.

In a typical composition, the reaction mixture obtained in step a) comprises the following compounds, in each case based on the total weight of the reaction mixture:
60 to 85% by weight of at least one compound (1),
5 to 15% by weight of at least one compound (II),
5 to 15% by weight of at least one of the compounds (III.1), (III.2) or (III.3),
0 to 10% by weight of at least one 3-methylbut-3-en-1-ol (IV),
0 to 5% by weight of at least one aldehyde (V)
0 to 5% by weight of at least one compound (VI),
2 to 10% by weight of water.

Preferably, the reaction mixture obtained in step a) comprises:
15 to 22% by weight of trans-(I),
45 to 65% by weight of cis-(I),
5 to 15% by weight of at least one compound (II),
5 to 15% by weight of at least one of the compounds (III.1), (III.2) or (III.3),
0 to 10% by weight of at least one 3-methylbut-3-en-1-ol (IV),
0 to 5% by weight of at least one aldehyde (V),
0 to 5% by weight of at least one compound (VI),
2 to 10% by weight of water,
in each case based on the total weight of the reaction mixture.

Preferably, the reaction mixture obtained in step a) comprises the 2-substituted 4-hydroxy-4-methyltetrahydropyrans of the formula (I) in the form of mixtures of the cis-diastereomers of the formula cis-(I) and of the trans-diastereomers of the formula trans-(I)

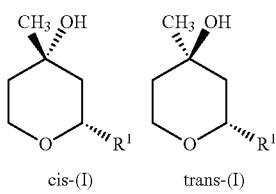

cis-(I)     trans-(I)

where the diastereomer ratio of the cis-diastereomer cis-(I) to the trans-diastereomer trans-(I) is preferably 65:35 to 95:5, particularly preferably 70:30 to 85:15, and $R^1$ has the meanings given above.

Preferably, the reaction mixture obtained in step a) comprises 2-isobutyl-4-hydroxy-4-methyltetrahydropyran in the form of mixtures of the cis-diastereomer of the formula cis-(I.a) and of the trans-diastereomer of the formula trans-(I.a)

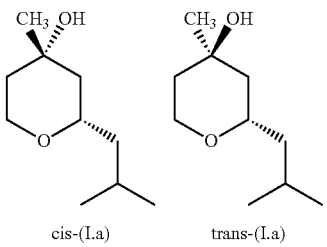

cis-(I.a)     trans-(I.a)

where the diastereomer ratio of the cis-diastereomer cis-(I.a) to the trans-diastereomer trans-(I.a) is preferably 65:35 to 95:5, particularly preferably 70:30 to 85:15.

On account of their particular odor properties, mixtures of this kind are suitable to a particular degree for use as aroma chemicals, for example as components with lily of the valley scent for producing fragrance compositions.

Acid Treatment

According to the invention, the reaction mixture from step a), prior to use in step b) and/or during use in step b), is brought into contact with an acidic ion exchanger and/or admixed with a strong acid.

In a first variant, the treatment of the reaction mixture from step a) with at least one acidic component takes place in homogeneous phase. In the event of the treatment according to the invention in homogeneous phase, the interacting components are present in the liquid phase. For this, a liquid reaction mixture from the reaction of 3-methylbut-3-en-1-ol (IV) with an aldehyde (V) or a liquid fraction obtained by distillative separation of such a reaction mixture can be admixed with a strong acid which, under the treatment conditions, is at least partially miscible with the reaction mixture or a fraction of the reaction mixture or is at least partially soluble in this.

In a second variant, the treatment of the reaction mixture from step a) with at least one acidic component takes place in heterogeneous phase. In the case of the treatment according to the invention in heterogeneous phase, the interacting components are generally present partly in the liquid phase and partly in the solid phase. For this, a liquid reaction mixture from the reaction of 3-methylbut-3-en-1-ol (IV) with an aldehyde (V) or a liquid fraction obtained by distillative separation of such a reaction mixture can be brought into contact with an acid present in solid form. Preferably, the acid for the treatment is used in solid phase in the form of a fixed bed. Preference is given to using an acidic ion exchanger for the treatment in solid phase.

Suitable strong acids and strong ion exchangers are the acidic catalyst specified above in step a). Reference is hereby made to these in their entirety.

Preferably, according to the first variant, the reaction mixture from step a), prior to use in step b), or a fraction obtained during the distillative separation in step b) is admixed with a strong acid. In a preferred embodiment, the reaction mixture from step a), prior to use in step b), is admixed with a strong acid. Alternatively, it is possible to admix the bottom of the distillative separation in step b) or, in the case of a multistage distillation, the bottom of the first distillation stage of the distillative separation in step b) with a strong acid.

Preferably, the reaction mixture from step a) is admixed, according to the first variant, with a strong acid which is selected from sulfuric acid, hydrochloric acid, methanesulfonic acid and p-toluenesulfonic acid.

Particularly preferably, the reaction mixture from step a) is admixed with sulfuric acid prior to use in step b).

Preferably, the reaction mixture from step a), prior to use in step b), is admixed with 1 to 250 ppm by weight, preferably with 2 to 100 ppm by weight, based on the total weight of the reaction mixture, of a strong acid. Alternatively, it is possible to admix the bottom of the distillative separation in step b) or, in the case of a multistage distillation, the bottom of the first distillation stage of the distillative separation in step b) with 1 to 250 ppm by weight, preferably with 2 to 100 ppm by weight, based on the total weight of the bottom product, of a strong acid. The quantitative data refers here to the pure acid. Of course it is possible and frequently preferred to use the acid in dilute form, specifically as aqueous solution.

According to the second variant described above, the reaction mixture from step a) is brought into contact with an acidic ion exchanger prior to use in step b).

The contacting with the acidic ion exchanger can take place discontinuously or continuously. Preference is given to continuous contacting.

Preferably, the contacting takes place at a temperature of from 30 to 80° C., particularly preferably from 40 to 70° C.

Suitable ion exchangers are the aforementioned strongly acidic cation exchangers. The use amount of acidic ion exchanger here is generally not critical. The reaction can accordingly be carried out either in the presence of catalytic amounts, or else in the presence of an excess, of a strongly acidic cation exchanger.

In particular, the reaction mixture from step a) is not subjected to a distillative separation before bringing it into contact with an acidic ion exchanger and/or admixing it with a strong acid.

Step b)

Preferably, in step b) of the process according to the invention, the reaction mixture from step a) is subjected to a distillative separation. Suitable devices for the distillative separation comprise distillation columns, such as tray columns which can be equipped with bubble caps, sieve plates, sieve trays, packings, packing bodies, valves, side take-off, etc., evaporators, such as thin-film evaporators, falling-film evaporators, forced-circulation evaporators, Sambay evaporators, etc., and combinations thereof.

The distillation columns can have separation-effective internals, which are preferably selected from separation trays, arranged packings, e.g. sheet-metal or fabric packings, such as Sulzer Mellapak®, Sulzer BX, Montz B1 or Montz A3 or Kühni Rombopak, or random beds of packings, such as e.g. Dixon rings, Raschig rings, high-flow rings or Raschig super rings. Arranged packings have proven to be particularly successful, preferably sheet-metal or fabric packings, with a specific surface area of from 100 to 750 $m^2/m^3$, in particular 250 to 500 $m^2/m^3$. They bring about high separation efficiencies coupled with low pressure losses.

Preferably, for the separation in step b), a device is used which comprises
 a feed column with rectification section situated above the feed point and stripping section situated below the feed point,
 an upper combining column communicating with the upper end of the rectification section and a lower combining column communicating with the lower end of the stripping section, and
 a discharge column communicating with the upper combining column and the lower combining column.

Preferably, the separation in step b) takes place by
i) introducing the reaction product from step a) into a feed column with rectification section situated above the feed point and stripping section situated below the feed point,
ii) providing an upper combining column communicating with the upper end of the rectification section and with condenser at the upper column end and a lower combining column communicating with the lower end of the stripping section and with heater at the lower column end,
iii) providing a discharge column communicating with the upper combining column and the lower combining column which has at least one side take-off,
iv) drawing off from the discharge column at the top or in the upper region compounds which boil more readily than the 2-substituted 4-hydroxy-4-methyltetrahydropyrans (I), drawing off, as at least one side take-off, at least some of the 2-substituted 4-hydroxy-4-methyltetrahydropyrans (I), and drawing off, in the bottom or in the lower region of the lower combining column, the 2-substituted 4-hydroxy-4-methyltetrahydropyrans (I) which have not been drawn off as side take-off and drawing off the compounds which have a higher boiling point than the 2-substituted 4-hydroxy-4-methyltetrahydropyrans (I).

In a preferred embodiment, the discharge removed from the discharge column at the top or in the upper region comprises:
 at least some or the total amount of the dioxane compound (II) present in the reaction product from step a),
 at least some or the total amount of the compounds (III.1), (III.2) and (III.3) present in the reaction product from step a),
 if present, unreacted 3-methylbut-3-en-1-ol of the formula (IV),
 if present, unreacted aldehyde (V),
 small amounts or no 2-substituted 4-hydroxy-4-methyltetrahydropyrans (I),
 water.

In a particularly preferred embodiment, 3-methylbut-3-en-1-ol of the formula (IV) and isovaleraldehyde (V) are used for the reaction in step a). The discharge removed from the discharge column at the top or in the upper region then comprises:
 at least some or the total amount of the dioxane compound (II) present in the reaction product from step a), in which $R^1$ is isobutyl,
 at least some or the total amount of the compounds (III.1), (III.2) and (III.3) present in the reaction product from step a), in which $R^1$ is isobutyl,
 if present, unreacted 3-methylbut-3-en-1-ol of the formula (IV),
 if present, unreacted isovaleraldehyde (V),
 small amounts or no 2-(2-methylpropyl)-4-hydroxy-4-methyltetrahydropyran of the formula (I.a),
 water.

The thus obtained top product can be subjected to a phase separation to separate off the majority of the water. Apart from such a phase separation, the thus obtained top product can generally be subjected to further processing without further work-up. This includes a hydrogenation to 2-substituted 4-methyltetrahydropyrans (VII) and specifically 2-(2-methylpropyl)-4-methyltetrahydropyran (dihydrorose oxide). If desired, the top product can be subjected to a further work-up to separate off at least some of the components different from the compounds (II), (III.1), (III.2) and (III.3). For this, the top product can be subjected e.g. to a further distillative separation.

In a preferred embodiment, one side stream is drawn off from the discharge column or two side streams are drawn off from the discharge column. In a specific embodiment, only one side stream is drawn off from the discharge column.

If, in step b), two or more discharges are removed which comprise 2-substituted 4-hydroxy-4-methyltetrahydropyrans (I), e.g. two different side take-offs or one side take-off and one bottom take-off, then these generally differ as regards the composition of the stereoisomers. Consequently, the isolation of a fraction enriched in cis-diastereomers compared to the reaction product from step a) and a fraction enriched in trans-diastereomers is possible. If the separation efficiency of the distillation apparatus used is adequate, at least one of the diastereomers can, if desired, be obtained in pure form.

The feed column, discharge column, upper combining column and lower combining column can be discrete design elements or be configured as a section or chamber of a distillation column which combines several functions. The expression "communicating columns" means that between them there is an exchange both of rising vapors as well as that of descending condensate.

In a preferred embodiment of the process according to the invention, the distillative separation in step b) takes place in an arrangement of distillation columns which comprises a dividing-wall column or an interconnection of at least two thermally coupled conventional distillation columns.

Dividing-wall columns are special distillation columns with at least one feed point and at least three removal points, in which the so-called rectification region is located between evaporator and condenser and in which some of the condensate formed in the condenser moves downwards in liquid form as reflux in countercurrent to the vapors rising from the evaporation device and which comprises, in a part region of the column, below and/or above the feed point at least one separation device (dividing wall) operating in the longitudinal direction for preventing crossmixing of liquid stream and/or vapor stream (steam stream) and which thus facilitate distillative separation of substance mixtures. The basic principle of dividing-wall columns has been known for a long time and is described for example in U.S. Pat. No. 2,471,134, in EP-A-0 122 367 or in G. Kaibel, Chem. Eng. Technol. Vol. 10, 1987, pages 92 to 98.

The general basic design of a dividing-wall column comprises at least one side feed point on one side of the dividing wall and at least three removal points, at least one of which is located on the other side of the dividing wall. Since in this design a crossmixing of liquid stream and/or vapor stream is prevented in the region of the dividing wall, it is possible to obtain the side products in pure form. In the event of separating multimaterial mixtures, this generally enables the number of distillation columns required overall to be reduced. Moreover, when using dividing-wall columns, investment costs as well as energy can be saved compared with a simple serial connection of two conventional distillation columns (see M. Knott, Process Engineering, Vol. 2, 1993, February, pages 33 to 34).

In the context of the invention, conventional distillation columns is the term used to denote all distillation columns which comprise no dividing wall. In thermally coupled conventional distillation columns, mass streams and energy streams are mutually exchanged. Consequently, compared with a simple serial connection of conventional distillation columns a considerable saving of energy is possible. A preferred alternative to the dividing-wall column is a connection of two thermally coupled distillation columns. An overview of various arrangements is given for example in G. Kaibel et al., Chem.-Ing.-Tech., Vol. 61, 1989, pages 16 to 25 and G. Kaibel et al., Gas Separation & Purification, Vol. 4, 1990, June, pages 109 to 114.

In a first preferred embodiment, a distillation column with a thermally coupled precolumn is used for the distillation, i.e. the discharge column, the upper combining column and the lower combining column are designed as a single-section distillation column, and the feed column is designed as a precolumn to the distillation column. In a second preferred embodiment, a distillation column with a thermally coupled post-column is used, i.e. the feed column, the upper combining column and the lower combining column are configured as a single-section distillation column, and the discharge column is configured as a post-column to the distillation column. Distillation columns with attached auxiliary columns are known and are described e.g. in Chem. Eng. Res. Des., Part A: Trans IChemE, March 1992, pp. 118-132, "The design and optimization of fully thermally coupled distillation columns".

It has proven to be favorable to remove at least some of the compounds which boil more easily than the 2-substituted 4-hydroxy-4-methyltetrahydropyrans (I) from the reaction product from step a) prior to introduction into the feed column. In a specific embodiment, for the distillative separation of the reaction product from step a), an arrangement of distillation columns is therefore used which comprises an upstream conventional distillation column and a downstream dividing-wall column and a downstream interconnection of two thermally coupled conventional distillation columns.

Preferably, for the distillative separation in step b)

b1) the reaction mixture from step a) is initially subjected to a separation in a conventional distillation column, where a first top product is obtained which is enriched in the dioxane compound (II) and the compounds (III.1), (III.2) and (III.3) and comprises essentially no compounds of the general formula (I), and a first bottom product is obtained which is depleted in the dioxane compound (II) and the compounds (III.1), (III.2) and (III.3) and comprises the majority of the compounds of the general formula (I), b2) the first bottom product from step b1) is subjected to a separation in a dividing-wall column or in an interconnection of two thermally coupled conventional distillation columns, where a second top product is obtained which comprises the compounds (II), (III.1), (III.2), (III.3) not present in the first top product, as well as optionally small amounts of the compounds of the general formula (I), a side stream is obtained which consists essentially of compound of the general formula (I), and a second bottom product is obtained which comprises the compounds of the general formula (I) which are not present in the top product and not present in the side stream.

Preferably, also in the aforementioned embodiment, in the compounds of the formulae (I), (II), (III.1), (III.2) and (III.3) $R^1$ is isobutyl.

The expression according to which the first top product comprises essentially no compounds of the general formula (I) means that the fraction of compounds of the general formula (I) in the first top product is at most 5% by weight, particularly preferably at most 2% by weight, in particular at most 1% by weight, specifically at most 0.1% by weight, based on the total weight of the first top product. In a special embodiment, the first top product comprises no compounds of the general formula (I).

The second top product can comprise for example 1 to 40% by weight, particularly preferably 2 to 30% by weight, in particular 5 to 25% by weight, specifically 10 to 20% by weight, of compounds of the general formula (I), based on the total weight of the second top product.

In a specific embodiment, the side stream consists only of compounds of the general formula (I).

In a further special embodiment, the second bottom product can comprise compounds which have a higher boiling point than the compounds of the general formula (I).

The fraction(s) obtained in step b) of the 2-substituted 4-hydroxy-4-methyltetrahydropyrans of the general formula (I) are advantageously characterized by a significantly reduced content, compared with the starting material, of components which do not adversely affect the odor impression. In particular, the occurrence of cheesy notes can be effectively presented. The fraction(s) obtained in step b) of the 2-substituted 4-hydroxy-4-methyltetrahydropyrans of the general formula (I) can in many cases be supplied for commercial use even without further work-up.

The fraction(s) obtained in step b) of the 2-substituted 4-hydroxy-4-methyltetrahydropyrans of the general formula (I) can if desired be subjected to a further work-up. For this, the fractions can be used individually or after a (partial) combining. The customary purification processes known to the person skilled in the art are suitable. These include, for example, a distillation, an extraction or a combination thereof.

A specific embodiment relates to a process in which the reaction mixture from step a) treated with acid is subjected to a distillative separation in an interconnection of distillation columns which comprises
  a conventional distillation column,
  a first dividing-wall column or a first interconnection of two thermally coupled conventional distillation columns, and
  a second dividing-wall column or a second interconnection of two thermally coupled conventional distillation columns.

A further special embodiment relates to a process in which the reaction mixture from step a) treated with acid
  is subjected to a first distillative separation, where a first top product is obtained which is enriched in the dioxane compound (II) and the compounds (III.1), (III.2) and (III.3) and comprises essentially no compounds of the general formula (I), and a first bottom product is obtained which is depleted in the dioxane compound (II) and the compounds (III.1), (III.2) and (III.3) and comprises the majority of the compounds of the general formula (I),
  the first bottom product is admixed with at least one base or subjected to a simple distillation, where the majority of the first bottom product is evaporated and then condensed,
  the first bottom product admixed with base or the condensate is subjected to a further distillative separation.

Suitable bases for addition to the first bottom product are alkali metal bases such as sodium hydroxide solution, potassium hydroxide solution, sodium carbonate, sodium hydrogen carbonate, potassium carbonate or potassium hydrogen carbonate and alkaline earth metal bases such as calcium hydroxide, calcium oxide, magnesium hydroxide or magnesium carbonate, and also amines. The base is particularly preferably selected from $Na_2CO_3$, $K_2CO_3$, $NaHCO_3$, $KHCO_3$, NaOH, KOH and mixtures thereof.

Preferably, the first bottom product following the addition of base has a pH in the range from 4 to 7.

In a specific embodiment, the first bottom product is brought into contact with a bed of at least one base.

In the context of the invention, a simple distillation is understood as meaning a distillation in which, unlike during the rectification or countercurrent distillation, some of the condensate is returned again countercurrently to the rising vapors of the boiling mixture, but where the bottom product is for the most part evaporated and then condensed. In a preferred embodiment, a Sambay evaporator is used.

The amount of first bottom product which is evaporated comprises preferably 60 to 99.9% by weight, particularly preferably 75 to 99% by weight, in particular 90 to 98% by weight, of the total amount of the bottom product.

The first bottom product admixed with base or the condensate is preferably subjected to a further distillative separation in a dividing-wall column or in an interconnection of two thermally coupled conventional distillation columns. Here, a second top product is preferably obtained which comprises the compounds (II), (III.1), (III.2), (III.3) not present in the first top product, and also optionally small amounts of the compounds of the general formula (I), a side stream which consists essentially of compound of the general formula (I) and a second bottom product which comprises the compounds of the general formula (I) which are not present in the top product nor in the side stream.

The compositions according to the invention and the compositions obtainable by the process according to the invention are particularly advantageously suitable as fragrance or for providing a fragrance.

In this connection, in addition to the 2-substituted 4-hydroxy-4-methyltetrahydropyrans of the general formula (I), the fraction obtained in step b), is enriched in at least one of the compounds (III.1), (III.2) or (III.3), can be subjected to further processing for the provision of a fragrance. Thus, as a result of hydrogenation of the compounds (III.1), (III.2) or (III.3), a hydrogenation product is obtained which comprises at least one 2-substituted 4-methyltetrahydropyran of the general formula (VII)

(VII)

in which
  $R^1$ is straight-chain or branched $C_1$-$C_{12}$-alkyl, straight-chain or branched $C_2$-$C_{12}$-alkenyl, unsubstituted or $C_1$-$C_{12}$-alkyl- and/or $C_1$-$C_{12}$-alkoxy-substituted cycloalkyl having in total 3 to 20 carbon atoms or unsubstituted or $C_1$-$C_{12}$-alkyl- and/or $C_1$-$C_{12}$-alkoxy-substituted aryl having in total 6 to 20 carbon atoms.

In particular, $R^1$ is isobutyl. This compound, referred to as dihydrorose oxide, is suitable on account of its particular odor properties with a rose scent-like character to a particular extent for use as aroma chemical and specifically for producing fragrance compositions.

This specific embodiment advantageously permits an integrated process for the simultaneous production of 2-substituted 4-hydroxy-4-methyltetrahydropyrans (I) and of 2-substituted 4-methyltetrahydropyrans (VII).

The present invention thus relates, in the context of a specifically preferred embodiment, to a process for the preparation and isolation of 2-(2-methylpropyl)-4-hydroxy-4-methyltetrahydropyran of the formula (I.a) and of dihydrorose oxide (VII.a)

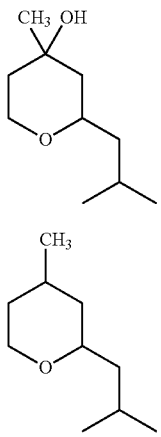

The compositions according to the invention can be diluted as required for use as fragrance with at least one solvent customary in this field of application. Examples of suitable solvents are: ethanol, dipropylene glycol or ethers thereof, phthalates, propylene glycols, or carbonates of diols, preferably ethanol. Water is also suitable as solvent for diluting the fragrance compositions according to the invention and can advantageously be used together with suitable emulsifiers.

On account of the structural and chemical similarity of the components, the fragrances obtained by the process according to the invention have high stability and durability.

The isomer mixtures obtainable by the process according to the invention of 2-(2-methylpropyl)-4-hydroxy-4-methyltetrahydropyran of the formula (I.a) are characterized by a pleasant lily of the valley scent. The isomer mixtures obtainable by the process according to the invention of 2-(2-methylpropyl)-4-methyltetrahydropyran of the formula (VII.a) (dihydrorose oxide) are characterized by a pleasant rose-like character.

The fragrances obtained by the process according to the invention are suitable for incorporation into cosmetic compositions as well as utility and consumer goods and/or compositions as are described in more detail below, it being possible to incorporate the fragrances into said products or else to apply them thereto. In the context of the entire present invention, an organoleptically effective amount here is to be understood in particular as meaning an amount which, upon use as directed, suffices to bring about a scent impression for the user or consumer.

All customary cosmetic compositions are suitable as cosmetic compositions. These are preferably perfume, eau de toilette, deodorants, soap, shower gel, bath gel, creams, lotions, sunscreens, compositions for the cleaning and care of hair such as hair shampoo, conditioner, hair gel, hair setting compositions in the form of liquids or mousses and further cleaning or care compositions for hair, compositions for decorative application on the human body, such as cosmetic sticks, for example lip sticks, lip care sticks concealing sticks (concealers), blusher, eye shadow pencils, lip liner pencils, eye liner pencils, eyebrow pencils, correction pencils, sunscreen sticks, anti-acne sticks and comparable products, as well as nail varnishes and further products for nail care.

The fragrances obtained by the process according to the invention are specifically suitable for use in perfumes, e.g. as eau de toilette, shower gels, bath gels and body deodorants.

They are furthermore suitable for the aromatization of consumer or utility goods into which they are incorporated and/or onto which they are applied and thereby impart a pleasant fresh green accent to them. Examples of consumer or utility goods are: air fresheners (air care), cleaning compositions or care compositions for textiles (specifically detergents, fabric softeners), textile treatment compositions such as, for example, ironing aids, scouring compositions, cleaning compositions, care compositions for treating surfaces, for example furniture, floors, kitchen appliances, glass panes and windows as well as screens, bleaches, toilet blocks, anti-limescale compositions, fertilizers, construction materials, mold removers, disinfectants, products for car or automobile care and more besides.

The examples below serve to illustrate the invention without limiting it in any way.

EXAMPLES

Gas chromatographic analyses were carried out according to the following method:
Column: DB WAX 30 m×0.32 mm;
FD 0.25 μm;
Injector temperature: 200° C.; detector temperature 280° C.;
Temperature program: Starting temp.: 50° C., at 3° C./min to 170° C.,
at 20° C./min to 230° C., 7 min isotherm;
Retention times: Isovaleraldehyde $t_R$=3.7 min
cis-Dihydrorose oxide $t_R$=8.4 min
trans-Dihydrorose oxide $t_R$=9.6 min
4,4-Dimethyl-2-isobutyl-1,3-dioxane $t_R$=11.9 min
Concentrations of the resulting crude products (% by weight) were ascertained by GC analysis with an internal standard.

Example 1 (According to the Invention)

A mixture of isovaleraldehyde (112.5 g, 1.31 mol), isoprenol (125 g, 1.45 mol) and 12.5 g of water was reacted in the presence of 50 g of the strongly acidic cation exchanger Amberlyst® 131, as described in example 1 of WO2011/154330.

The resulting crude product had the following composition:
19.5 GC area % trans-pyranol (I)
56.1 GC area % cis-pyranol (I)
9.0 GC area % dihydropyran isomers 1-3
8.2 GC area % 1,3-dioxane
0.7 GC area % isovaleraldehyde
1.3 GC area % isoprenol
0.5 GC area % acetal
8.7% water (Karl-Fischer method)

The crude product was subjected to a distillative separation in an arrangement of a conventional distillation column and a dividing-wall column. The laboratory apparatus consisted of two laboratory columns. The separation efficiency of the first column corresponds to approximately 15 theoretical trays. For the separation of the two phases of the top condensate, a glass phase separator was incorporated. The lower aqueous phase was discharged in a level-controlled manner. The upper organic phase was divided with the help of a reflux divider in a fixed ratio, with some being separated off as top product and the remainder being returned to the column at the top. The feed to the column was carried out between the two column units. The feed stream was conveyed at room temperature. The flow rate was 1000 g/h.

10 ppm by weight of sulfuric acid as 1% strength solution in water were added to the crude product.

The column was operated at a top pressure of 50 mbar and a reflux amount of 360 g/h. Here, a pressure loss of about 3.1 mbar was established. At the top of the column, a temperature of 70° C. was measured, and in the bottom a temperature of 131° C. was measured. The bottom discharge amount was fixed at 776 g/h. The top discharge amount was 131 g/h.

The fractions obtained were analyzed by gas chromatography with the help of a standard GC. Gas chromatographic analyses were carried out according to the following method:
Column: DB WAX 30 m×0.32 mm; FD 0.25 μm; Inj. 200° C., Det. 280° C.; 50° C., 3°/' to 170° C.-20°/' to 230° C.-7 min isoth., $t_R$=min; $t_R$ (isovaleraldehyde): 3.8; $t_R$ (dihydropyranisomers): 10.1; 12.0; 12.4; $t_R$ (isoprenol): 10.7; $t_R$ (1,3-dioxane): 12.2; $t_R$ (acetal): 24.8; $t_R$ (trans-pyranol): 28.5; $t_R$ (cis-pyranol): 30.0; concentrations of the resulting crude products (% by weight) were determined by GC analysis by means of an internal standard.

The top stream drawn off from the phase separator at the top of the column comprised:
1.2% water (Karl-Fischer method)
3.8 GC area % isovaleraldehyde
44.3 GC area % dihydropyran isomers 1-3
8.9 GC area % isoprenol
38.9 GC area % 1,3-dioxane The following were found in the bottom discharge column
0.04 GC area % isoprenol
2.37 GC area % dihydropyran isomers
2.1 GC area % 1,3-dioxane
23.5 GC area % trans-pyranol
67.4 GC area % cis-pyranol.

The distillation yield as regards cis- and trans-pyranol was 100%.

The second laboratory column was configured as a dividing-wall column. The separation efficiency in the dividing wall region was about 32 theoretical plates. The total number of theoretical plates including the dividing-wall region was about 50. The feed was added at the height of the middle of the dividing wall section. The feed stream used was the mixture from the bottom discharge of the first column. The feed flow rate was 302.4 g/h. The column was operated at a top pressure of 10 mbar and a reflux of 400 g/h. At the top of the column, a temperature of 72° C. was measured and in the bottom a temperature of 124° C. (±0.5 K) was measured. The bottom discharge was adjusted to 14 g/h (±1 g/h) and the distillate removal was adjusted to 26 g/h (±1 g/h).

The reflux ratio was thus about 15:1. The liquid was divided above the dividing wall in a ratio of 1:2 (feed section:removal section). On the side of the dividing wall opposite the addition side, a liquid side take-off was removed at the same height as the feed stream. The flow rate was fixed at 261 g/h.

The pure product obtained at the side take-off comprised:
24.6 GC area % trans-pyranol and
74.7 GC area % cis-pyranol
Olfactory assessment of the pure product:
Smelling strip test 30 min: corresponds to the desired specification Gas space test: corresponds to the desired specification
The distillation yield as regards cis- and trans-pyranol was about 97.5%.

Example 2 (Comparison)

The procedure was as in example 1 but no sulfuric acid was added to the crude product used for the distillation.
The pure product obtained at the side take-off of the dividing-wall column comprised:
25.5 GC area % trans-pyranol and
73.6 GC area % cis-pyranol
Olfactory evaluation of the pure product;
Smelling strip test 30 min: does not correspond to the specification
Gas space test: does not correspond to the specification
The distillation yield as regards cis- and trans-pyranol was about 98.0%.

The invention claimed is:
1. A process for the preparation of 2-substituted 4-hydroxy-4-methyltetrahydropyrans of the formula (I)

in which
R$^1$ is straight-chain or branched C$_1$-C$_{12}$-alkyl, straight-chain or branched C$_2$-C$_{12}$-alkenyl, unsubstituted or C$_1$-C$_{12}$-alkyl- and/or C$_1$-C$_{12}$-alkoxy-substituted cycloalkyl having in total 3 to 20 carbon atoms or unsubstituted or C$_1$-C$_{12}$-alkyl- and/or C$_1$-C$_{12}$-alkoxy-substituted aryl having in total 6 to 20 carbon atoms,
which comprises the following steps)
a) reacting 3-methylbut-3-en-1-ol of the formula (IV)

with an aldehyde of the formula (V)

R$^{11}$—CHO           (V)

in which
R$^{11}$ is straight-chain or branched C$_1$-C$_{12}$-alkyl, straight-chain or branched C$_2$-C$_{12}$-alkenyl, unsubstituted or C$_1$-C$_{12}$-alkyl- and/or C$_1$-C$_{12}$-alkoxy-substituted cycloalkyl having in total 3 to 20 carbon atoms or unsubstituted or C$_1$-C$_{12}$-alkyl- and/or C$_1$-C$_{12}$-alkoxy-substituted aryl having in total 6 to 20 carbon atoms,
in the presence of an acidic catalyst, where a reaction mixture is obtained which comprises at least one 2-substituted 4-hydroxy-4-methyltetrahydropyran of the formula (I),
b) the reaction mixture from step a) is subjected to a distillative separation to give at least one fraction enriched in the 2-substituted 4-hydroxy-4-methyltetrahydropyrans of the formula (I), and
c) where the reaction mixture from step a), prior to use in step b) and/or during use in step b), is brought into contact with an acidic ion exchanger and/or admixed with 1 to 250 ppm, based on the weight of the reaction mixture, of a strong acid.

2. The process according to claim 1, wherein the reaction mixture from step a), during the use in step b) is brought into contact with an acidic ion exchanger and/or admixed with a strong acid.

3. The process according to claim 1, wherein a fraction obtained during the distillative separation in step b), is admixed with a strong acid.

4. The process according to claim 1, wherein the bottom of the distillative separation in step b) or, in the case of a multi-stage distillation, the bottom of the first distillation stage of the distillative separation in step b) is admixed with a strong acid.

5. The process according to claim 1, where a strong acid is used which is selected from sulfuric acid, hydrochloric acid, methanesulfonic acid and p-toluenesulfonic acid.

6. The process according to claim 1, where sulfuric acid is used as strong acid.

7. The process according to claim 1, where the reaction mixture from step a), prior to use in step b), is admixed with 1 to 250 ppm by weight based on the total weight of the reaction mixture, of a strong acid.

8. The process according to claim 1, wherein the bottom of the distillative separation in step b) or, in the case of a multi-stage distillation, the bottom of the first distillation stage of the distillative separation in step b) is admixed with 1 to 250 ppm by weight, based on the total weight of the bottom product, of a strong acid.

9. The process according to claim 1, where, in step a), a reaction mixture is obtained which comprises at least one 2-substituted 4-hydroxy-4-methyltetrahydropyran of the formula (I),
at least one dioxane compound (II)

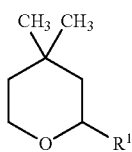

(II)

and at least one of the compounds (III.1), (III.2) or (III.3)

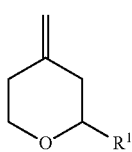

(III.1)

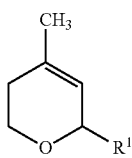

(III.2)

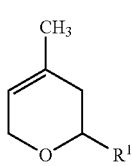

(III.3)

in which
$R^1$ is straight-chain or branched $C_1$-$C_{12}$-alkyl, straight-chain or branched $C_2$-$C_{12}$-alkenyl, unsubstituted or $C_1$-$C_{12}$-alkyl- and/or $C_1$-$C_{12}$-alkoxy-substituted cycloalkyl having in total 3 to 20 carbon atoms or unsubstituted or $C_1$-$C_{12}$-alkyl- and/or $C_1$-$C_{12}$-alkoxy-substituted aryl having in total 6 to 20 carbon atoms.

10. The process according to claim 6, where, in step a), a reaction mixture is obtained which additionally comprises at least one compound which is selected from:
3-methylbut-3-en-1-ols of the formula (IV)
aldehydes of the formula (V)
acetals of the general formula (VI)

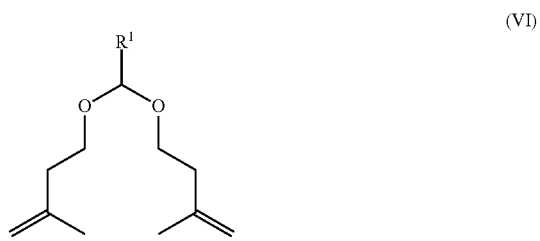

(VI)

in which
$R^1$ is straight-chain or branched $C_1$-$C_{12}$-alkyl, straight-chain or branched $C_2$-$C_{12}$-alkenyl, unsubstituted or $C_1$-$C_{12}$-alkyl- and/or $C_1$-$C_{12}$-alkoxy-substituted cycloalkyl having in total 3 to 20 carbon atoms or unsubstituted or $C_1$-$C_{12}$-alkyl- and/or $C_1$-$C_{12}$-alkoxy-substituted aryl having in total 6 to 20 carbon atoms.

11. The process according to claim 1, where the reaction mixture obtained in step a) comprises
60 to 85% by weight of at least one compound (I),
5 to 15% by weight of at least one compound (II),
5-15% by weight of at least one of the compounds (III.1), (III.2) or (III.3),
0-10% by weight of at least one 3-methylbut-3-en-1-ol (IV),
0-5% by weight of at least one aldehyde (V), and
0-5% by weight of at least one compound (VI),
based on the total weight of the reaction mixture.

12. The process according to claim 1, where the radical $R^1$ is isobutyl or phenyl.

13. The process according to claim 1, in which the reaction in step a) takes place in the presence of an acidic catalyst which is selected from hydrochloric acid, sulfuric acid, methanesulfonic acid, p-toluenesulfonic acid and strongly acidic cation exchangers.

14. The process according to claim 1, in which the reaction in step a) is carried out in the presence of a strongly acidic cation exchanger and further in the presence of added water.

15. The process according to claim 1, where, for the separation in step b), a device is used which comprises
a feed column with rectification section situated above the feed point and stripping section positioned below the feed point,
an upper combining column communicating with the upper end of the rectification section and a lower combining column communicating with the lower end of the stripping section, and
a discharge column communicating with the upper combining column and the lower combining column.

16. The process according to claim 1, where the distillative separation in step b) takes place in an arrangement of distillation columns which comprises a dividing-wall column or an interconnection of at least two thermally coupled conventional distillation columns.

17. The process according to claim 1, where, for the distillative separation of the reaction product from step a), an arrangement of distillation columns is used which comprises an upstream conventional distillation column and a downstream dividing-wall column or a downstream interconnection of two thermally coupled distillation columns.

18. The process according to claim 1, where the distillative separation in step b) comprises
b1) subjecting the reaction mixture from step a) which comprises at least one 2-substituted 4-hydroxy-4-methyltetrahydropyran of the formula (I),
at least one dioxane compound (II)

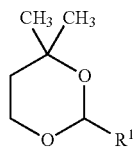

(II)

and at least one of the compounds (III.1), (III.2) or (III.3)

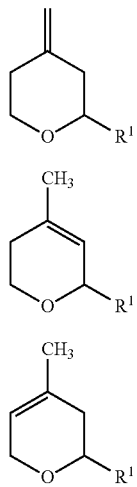

(III.1)

(III.2)

(III.3)

in which
$R^1$ is straight-chain or branched $C_1$-$C_{12}$-alkyl, straight-chain or branched $C_2$-$C_{12}$-alkenyl, unsubstituted or $C_1$-$C_{12}$-alkyl- and/or $C_1$-$C_{12}$-alkoxy-substituted cycloalkyl having in total 3 to 20 carbon atoms or unsubstituted or $C_1$-$C_{12}$-alkyl- and/or $C_1$-$C_{12}$-alkoxy-substituted aryl having in total 6 to 20 carbon atoms,
to a separation in a distillation column, where a first top product is obtained which is enriched in the dioxane compound (II) and the compounds (III.1), (III.2) and (III.3) and consists essentially of no compounds of the formula (I), and a first bottom product is obtained which is depleted in the dioxane compound (II) and the compounds (III.1), (III.2) and (III.3) and comprises the majority of the compounds of the formula (I),
b2) subjecting the first bottom product from step b1) to a separation in a dividing-wall column or in an interconnection of two thermally coupled conventional distillation columns, where a second top product is obtained which comprises the compounds (II), (III.1), (III.2), (III.3) not present in the first top product, as well as optionally small amounts of the compounds of the formula (I), a side stream is obtained which consists essentially of compound of the formula (I), and a second bottom product is obtained which comprises the compounds of the formula (I) which are not present in the top product and not present in the side stream.

19. The process according to claim 1, comprising subjecting the reaction mixture treated with acid from step a) which comprises
at least one 2-substituted 4-hydroxy-4-methyltetrahydropyran of the formula (I),
at least one dioxane compound (II)

(II)

and at least one of the compounds (III.1), (III.2) or (III.3)

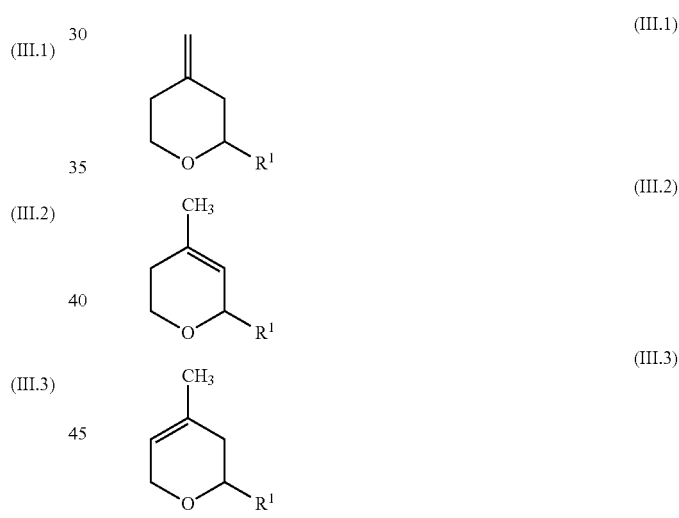

(III.1)

(III.2)

(III.3)

in which
$R^1$ is straight-chain or branched $C_1$-$C_{12}$-alkyl, straight-chain or branched $C_2$-$C_{12}$-alkenyl, unsubstituted or $C_1$-$C_{12}$-alkyl- and/or $C_1$-$C_{12}$-alkoxy-substituted cycloalkyl having in total 3 to 20 carbon atoms or unsubstituted or $C_1$-$C_{12}$-alkyl- and/or $C_1$-$C_{12}$-alkoxy-substituted aryl having in total 6 to 20 carbon atoms,
to a first distillative separation, where a first top product is obtained which is enriched in the dioxane compound (II) and the compounds (III.1), (III.2) and (III.3) and consists essentially of no compounds of the formula (I), and a first bottom product is obtained which is depleted in the dioxane compound (II) and the compounds (III.1), (III.2) and (III.3) and comprises the majority of the compounds of the formula (I),
admixing the first bottom product with at least one base or subjecting the first bottom product to a simple distillation, where the majority of the first bottom product is evaporated and then condensed, subjecting the first bottom product admixed with base or the condensate to a further distillative separation.

20. The process according to claim 1, where is isobutyl.

21. The process according to claim 1 wherein the compound of formula (I) is 2-isobutyl-4-hydroxy-4-methyltetrahydropyran.

22. The process according to claim 1, wherein the reaction mixture from step a), prior to use in step b) and/or during use in step b), is brought into contact with a strong acid.

* * * * *